United States Patent
Huang et al.

(10) Patent No.: US 11,915,818 B2
(45) Date of Patent: Feb. 27, 2024

(54) SYSTEM AND METHOD FOR ASSESSING EXTUBATION

(71) Applicants: Changhua Christian Medical Foundation Changhua Christian Hospital, Changhua (TW); National Chung Hsing University, Taichung (TW)

(72) Inventors: Kuo-Yang Huang, Changhua (TW); Ying-Lin Hsu, Taichung (TW); Yin-Tzer Shih, Taichung (TW)

(73) Assignee: Changhua Christian Medical Foundation Changhua Christian Hospital, Changhua (TW)

( * ) Notice: Subject to any disclaimer, the term of this patent is extended or adjusted under 35 U.S.C. 154(b) by 105 days.

(21) Appl. No.: 17/827,011

(22) Filed: May 27, 2022

(65) Prior Publication Data

US 2022/0406436 A1     Dec. 22, 2022

(30) Foreign Application Priority Data

Jun. 11, 2021  (TW) .................................. 110121360

(51) Int. Cl.
  *G16H 20/40*     (2018.01)
  *G16H 10/60*     (2018.01)
  (Continued)

(52) U.S. Cl.
  CPC ........... *G16H 20/40* (2018.01); *A61B 5/0871* (2013.01); *A61B 5/7267* (2013.01);
  (Continued)

(58) Field of Classification Search
  None
  See application file for complete search history.

(56) References Cited

U.S. PATENT DOCUMENTS

| 9,785,745 B2 | 10/2017 | Bravi et al. |
| 2020/0005900 A1* | 1/2020 | Cha ........................ G16H 10/40 |

FOREIGN PATENT DOCUMENTS

| CN | 106659410 A | 5/2017 |
| CN | 107529993 A | 1/2018 |

(Continued)

OTHER PUBLICATIONS

Search report for TW110121360, dated Apr. 7, 2022, Total of 1 page.

(Continued)

*Primary Examiner* — K. Wong
(74) *Attorney, Agent, or Firm* — Apex Juris, pllc; Hilde Coeckx

(57) ABSTRACT

A system for assessing extubation includes a respiratory assistance device, an artificial intelligence platform, and a hospital information system. The respiratory assistance device is adapted to communicate with a trachea of a patient. The artificial intelligence platform includes a prediction module. A method for assessing extubation includes the following steps. Measured values of respiratory parameters of the patient are recorded by the respiratory assistance device. The recorded times and the measured values of the respiratory parameters corresponding to each of the recording times are transmitted to the artificial intelligence platform. The prediction module analyzes the measured values of respiratory parameters within a predetermined time period according to a prediction model to generate a prediction result. The prediction result is transmitted to the hospital information system and is recorded into a medical record of the patient. With such design, a reference for extubation assessment that is more accurate is provided.

17 Claims, 2 Drawing Sheets

(51) Int. Cl.
*A61B 5/00* (2006.01)
*A61M 16/00* (2006.01)
*A61B 5/087* (2006.01)
*A61M 16/04* (2006.01)

(52) U.S. Cl.
CPC ......... *A61B 5/7275* (2013.01); *A61M 16/024* (2017.08); *A61M 16/04* (2013.01); *G16H 10/60* (2018.01)

(56) References Cited

FOREIGN PATENT DOCUMENTS

| | | |
|---|---|---|
| CN | 112675393 A | 4/2021 |
| TW | 200720955 A | 6/2007 |

OTHER PUBLICATIONS

English abstracts for CN112675393, Total of 1 page.
English abstracts for TW200720955, Total of 1 page.
English abstracts for CN107529993, Total of 1 page.
English abstracts for CN106659410 Total of 1 page.

\* cited by examiner

SYSTEM AND METHOD FOR ASSESSING EXTUBATION

BACKGROUND OF THE INVENTION

Technical Field

The present invention relates generally to an assessment of weaning off a respiratory assistance device, and more particularly to a system and a method for assessing extubation.

Description of Related Art

Intubation is to insert an endotracheal tube into a trachea of a patient through mouth or nose of a patient, so that the respiratory assistance device can communicate with the trachea of the patient through the endotracheal tube, thereby establishing an airway for providing oxygen or air to maintain breathing. After the doctor assesses the conditions of the patient and determines the condition is improved, a training facilitating weaning from the respiratory assistance device will be started. After the patient is trained for a period of time, the doctor will assess the patient again to determine the readiness for extubation of the patient. When the doctor determines that the patient is ready for extubation and can spontaneously breathe, the doctor removes the endotracheal tube from the patient to allow the patient to be liberated from the respiratory assistance device.

So far, in clinical practice, an index used for assessing extubation is the rapid shallow breathing index (RSBI). The rapid shallow breathing index is measured before extubation. When the RSBI is smaller than and equal to 105, an outcome of the extubation is more likely to have success, which means that the patient does not need reintubation within 48 hours after extubation. Generally, when the RSBI is smaller than and equal to 105, successful extubation has 92% chance. However, when the RSBI is greater than 105, which is a condition that is determined not ready for extubation, the successful extubation still has 53% chance. In other words, when the extubation assessment is merely based on the rapid shallow breathing index (RSBI), over a half amount of the patients that are determined not ready for extubation could be successfully weaned off from the respiratory assistance device (namely, successfully extubated).

Thus, the extubation assessment merely based on the rapid shallow breathing index (RSBI) is not accurate.

BRIEF SUMMARY OF THE INVENTION

In view of the above, the primary objective of the present invention is to provide a system for assessing extubation and a method for assessing extubation, which could present a reference that is calculated based on a breathing status for a period of time before extubation, thereby providing a doctor a more reliable reference for extubation assessment.

The present inventive subject matter provides a system for assessing extubation, including a respiratory assistance device, an artificial intelligence platform, and a hospital information system. The respiratory assistance device is adapted to communicate with a trachea of a patient via an endotracheal tube, wherein the respiratory assistance device continuously records measured values of a plurality of respiratory parameters of the patient at predetermined time intervals. The artificial intelligence platform receives recorded times and measured values of the respiratory parameters corresponding to each of the recorded times, wherein the artificial intelligence platform includes a prediction module, and the prediction module analyzes the measured values of the respiratory parameters within a predetermined time period according to the at least one prediction model and generates at least one prediction result. The at least one prediction result comprises one of the success status and a failure status. The hospital information system receives the at least one prediction result and records the at least one prediction result that is received into a medical record of the patient.

The present inventive subject matter provides a method for assessing extubation, comprising the following steps.

Continuously record measured values of a plurality of respiratory parameters of the patient at predetermined time intervals.

Transmit the recorded time and the measured values of a plurality of respiratory parameters corresponding to the recorded time to artificial intelligence platform. Then, analyze the measured values of the respiratory parameters within a predetermined time period according to at least one prediction model to generate at least one prediction result by the prediction module, wherein the at least one prediction result comprises one of the success status and a failure status.

Transmit the at least one prediction result to the hospital information system, wherein the hospital information system records the at least one prediction result that is received into a medical record of the patient.

With such design, an artificial intelligence prediction model is adopted to analyze the recorded data of the respiratory parameters of the patients to generate the prediction result. Comparing the prediction result to the conventional index for extubation assessment, the prediction result could accurately reflect the breathing status of the patient for a period before extubation, thereby providing a prediction result that is more accurate for the doctor's reference. Thus, for the doctor, the time to make a decision could be accelerated, and for the patient, the time to be intubated could be shortened.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
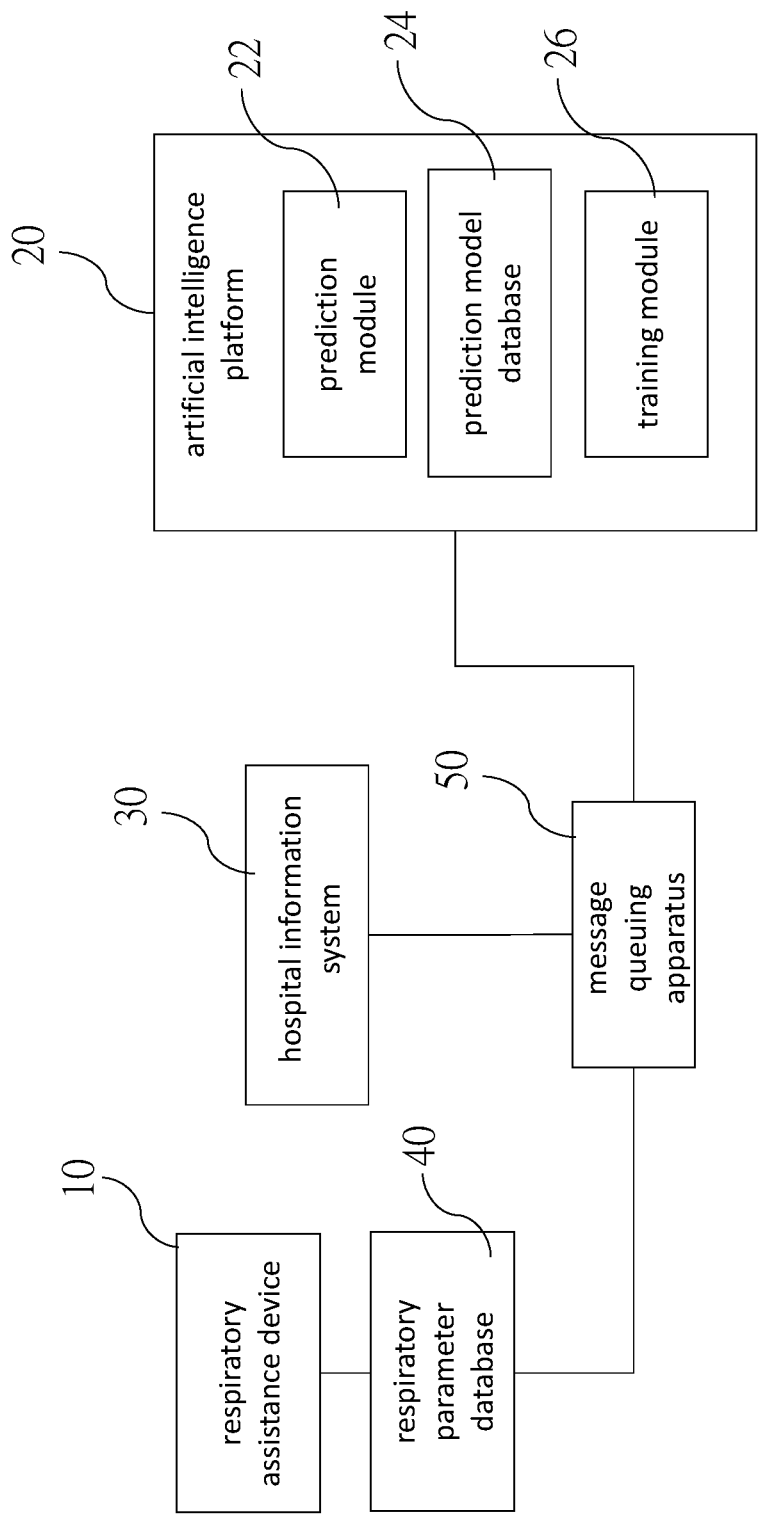
FIG. 1 is a schematic view of the system for assessing extubation of an embodiment according to the present invention.
Figure 2:
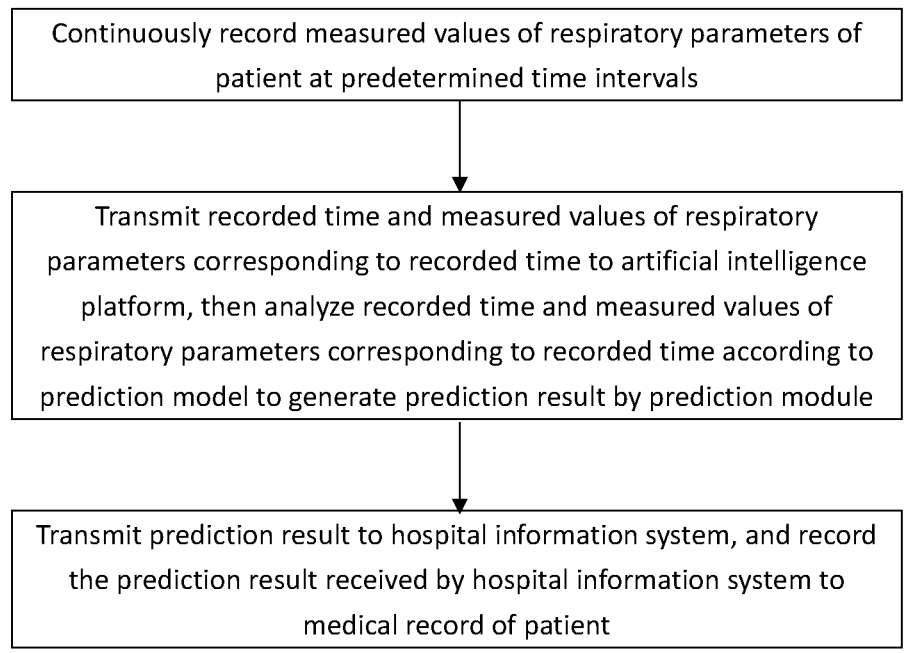
FIG. 2 is a flowchart of the method for assessing extubation of the embodiment according to the present invention.

As illustrated in FIG. 1, a system for assessing extubation of an embodiment according to the present invention is adapted to assess an intubated patient to determine whether the patient is ready for extubation. The system for assessing extubation includes a respiratory assistance device 10, an artificial intelligence platform 20, and a hospital information system (HIS) 30. As illustrated in FIG. 2, a method for assessing extubation of an embodiment according to the present invention is presented.

The respiratory assistance device 10 is adapted to pump air or oxygen into a trachea of the patient and help the patient breathe. The respiratory assistance device 10 is attached to an endotracheal tube that is inserted into the trachea of the patient to communicate with the trachea of the patient. Except for pumping oxygen, the respiratory assistance device 10 continuously monitors and records a plurality of respiratory parameters of the patient, wherein the plurality of respiratory parameters includes at least two respiratory parameters, namely tidal volume (Vte) and respiratory rate (RR). Additionally, the plurality of respiratory parameters could further include at least one of peak airway pressure (Ppeak), mean airway pressure (Pmean), positive end-expiratory pressure (PEEP), and fraction of inspiration $O_2$ ($FiO_2$).

The respiratory assistance device 10 continuously records measured values of the respiratory parameters at predetermined time intervals. For example, the respiratory parameters are recorded once at 1-minute intervals, and recorded times and the measured values of the respiratory parameters corresponding to each of the recorded times are transmitted to a respiratory parameter database 40 to store. It is worthy to note that the recorded time is a time when the measured values of the respiratory parameters are recorded.

In an embodiment, there is a plurality of respiratory assistance devices 10 provided for several patients. Each of the plurality of respiratory assistance devices 10 is put on one of the patients. Each of the respiratory assistance devices 10 transmits every recorded time and every measured values of respiratory parameters corresponding to each of the recorded times to the respiratory parameter database 40 for storing.

Additionally, in the current embodiment, the system optionally includes a message queuing apparatus 50 that is respectively connected to the respiratory assistance device 10, the artificial intelligence platform 20, and the hospital information system 30. The message queuing apparatus 50 is a center of message transmission. In the current embodiment, the message queuing apparatus 50 is connected to the respiratory parameter database 40 to receive the recorded time and the measured values of the respiratory parameters corresponding to the recorded time. Practically, the message queuing apparatus 50 could be directly connected to the respiratory assistance device 10. When the message queuing apparatus 50 is directly connected to the respiratory assistance device 10, the respiratory assistance device 10 transmits the recorded time and the measured values of the respiratory parameters corresponding to the recorded time to the message queuing apparatus 50.

The artificial intelligence platform 20 is adapted to receive the recorded time and the measured values of the respiratory parameters corresponding to the recorded time. In the current embodiment, the artificial intelligence platform 20 is run on a server and is connected to the message queuing apparatus 50. The artificial intelligence platform 20 obtains the recorded time and the measured values of the respiratory parameters corresponding to the recorded time from the message queuing apparatus 50. In other embodiment, the artificial intelligence platform 20 could be directly connected to the respiratory parameter database 40 or the respiratory assistance device 10. The artificial intelligence platform 20 includes a prediction module 22 and a prediction model database 24. The prediction model database 24 stores at least one prediction model. The prediction module 22 analyzes the respiratory parameters within a predetermined time period according to the at least one prediction model and generates at least one prediction result, wherein the at least one prediction result includes one of a success status and a failure status. The success status means that the patient does not need for reintubation within 48 hours after extubation. The failure status means that the patient needs for reintubation within 48 hours after extubation. Additionally, the prediction result could further include a degree of confidence that corresponds to the success status, and/or a degree of confidence that corresponds to the failure status, wherein the degree of confidence could be presented as a percentage. In the current embodiment, the degree of confidence corresponding to the success status means a chance of successful extubation, and the degree of confidence corresponding to the failure status means a chance of fall extubation. When the degree of confidence of either the success status or the failure status is higher, the success status or the failure status is more accurate, which is more reliable and referable.

In the current embodiment, the at least one prediction model that is stored in the prediction model database 24 includes two prediction models, wherein each of the two prediction models analyzes to calculate the measured values of the respiratory parameters within the predetermined time period based on one of the two algorithms, namely convolutional neural network (CNN) and Long short-term memory (LSTM), thereby generating two prediction results, respectively.

The predetermined time period could be set in a range of 1 to 3 hours. For example, when the predetermined time period is 3 hours, the predetermined time is 1 minute. The prediction module 22 analyzes 180 recorded entries of the respiratory parameters within the latest 3 hours according to the convolutional neural network and the long short-term memory, thereby obtaining two prediction results.

In other embodiments, the prediction module 22 could merely adopt one prediction model. The prediction module 22 could analyze recorded entries of the respiratory parameters within the predetermined time period according to the prediction model, namely either the convolutional neural network or the long short-term memory to obtain one prediction result.

In the current embodiment, the artificial intelligence platform 20 further includes a training module 26 adapted to conduct a model training process. In the model training process, the training module 26 is adapted to train each of the prediction models by using a plurality of training data to improve the accuracy of each of the prediction models. The training data includes measured values of respiratory parameters of reference patients which are measured by the respiratory assistance device 10 and extubation outcomes of the reference patients. More specifically, the training data includes a plurality of historical data of respiratory parameters of the reference patients within a reference time period and the extubation outcomes of the reference patients. The reference time period could be set in a range of 1 to 3 hours before extubation. The historical data of respiratory parameters includes every recorded entry of the respiratory parameters at each intervals that are obtained by the respiratory assistance device 10 attached to each of the reference patients. The respiratory parameters of the reference patients and the respiratory parameters for assessing extubation should be the same. In other words, the respiratory parameters of the reference patients include at least tidal volume and respiratory rate. Alternatively, the respiratory parameters of the reference patients further include one of peak airway pressure, mean airway pressure, positive end-expiratory pressure, fraction of inspiration $O_2$. The extubation outcome includes the success status or the failure status which is an outcome of each of the reference patients after extubation. The success status means that the patient does not need for reintubation within 48 hours after extubation. The failure status means that the patient needs for reintubation within 48 hours after extubation.

Table 1 shows the accuracy of the prediction result calculated by each of the two prediction models of the prediction module 22, wherein the two prediction models are trained by the training data obtained from 198 reference patients. The training data includes the historical data of two respiratory parameters (tidal volume and respiratory rate) of the 198 reference patients within different predetermined time periods (namely, 3 hours, 2 hours, and 1 hour) and the extubation outcome of each of the 198 reference patients. The accuracy of the prediction result is verified by the historical data of the respiratory parameters (tidal volume and respiratory rate) of another 50 reference patients within different predetermined time periods (namely, 3 hours, 2 hours, and 1 hour) and the extubation outcome of each another 50 reference patients, which are different from the 198 reference patients. Table 1 shows the accuracy of the prediction results of the 50 reference patients that are calculated by each of the two algorithms (including CNN and LSTM). The accuracy is a percentage of the prediction results of the 50 reference patients that are consistent with the extubation outcome of the 50 reference patients. For example, when the prediction results (which is either the success status or the failure status) of the 50 reference patients are obtained by analyzing the historical data of the respiratory parameters (tidal volume and respiratory rate) within 1 hour before extubation according to CNN, comparing the prediction results with the extubation outcomes, the accuracy of prediction is 79.2%. The accuracy of the prediction results calculated according to CNN is higher than 79.2%, and the accuracy of the prediction results calculated according to LSTM is higher than 87.2% and reaches 89.6%.

TABLE 1

The accuracy of the prediction result obtained by analyzing two respiratory parameters within different time periods according to each of the two prediction models is shown, respectively.

| Prediction Model | 3 hours | 2 hours | 1 hour |
| --- | --- | --- | --- |
| CNN | 82.8% | 85.6% | 79.2% |
| LSTM | 89.6% | 87.2% | 87.2% |

Table 2 shows the accuracy of the prediction result calculated by one of the two prediction models of the prediction module 22, wherein the two prediction models are trained by the training data obtained from the 198 reference patients. The training data includes the historical data of six respiratory parameters (tidal volume, respiratory rate, peak airway pressure, mean airway pressure, positive end-expiratory pressure, and fraction of inspiration $O_2$) of the 198 reference patients within different predetermined time periods (namely, 3 hours, 2 hours, and 1 hour) and the extubation outcome of each of the 198 reference patients. The accuracy of the prediction result is verified by the historical data of the six respiratory parameters (tidal volume, respiratory rate, peak airway pressure, mean airway pressure, positive end-expiratory pressure, and fraction of inspiration $O_2$) of another 50 reference patients within different predetermined time periods (namely, 3 hours, 2 hours, and 1 hour) and the extubation outcome of each another 50 reference patients, which are different from the 198 reference patients. Table 2 shows the accuracy of the prediction results of the 50 reference patients that are calculated by each of the two algorithms (including CNN and LSTM). The accuracy is a percentage of the prediction results of the 50 reference patients that are consistent with the extubation outcome of the 50 reference patients. For example, when the prediction results (which is either the success status or the failure status) of the 50 reference patients are obtained by analyzing the historical data of the six respiratory parameters (tidal volume, respiratory rate, peak airway pressure, mean airway pressure, positive end-expiratory pressure, and fraction of inspiration $O_2$) within 1 hour before extubation according to CNN, comparing the prediction results with the extubation outcomes, the accuracy of prediction is 76%. The accuracy of the prediction results calculated according to CNN is higher than 76%, and the accuracy of the prediction results calculated according to LSTM is higher than 82.8 and is able to reach 92%.

TABLE 2

The accuracy of the prediction result obtained by analyzing six respiratory parameters within different time periods according to each of the two prediction models is shown, respectively.

| Prediction Model | 3 hours | 2 hours | 1 hour |
| --- | --- | --- | --- |
| CNN | 84% | 81.6% | 76% |
| LSTM | 92% | 82.8% | 89.2% |

As shown in Table 1 and Table 2, the prediction model of the current embodiment could accurately predict the extubation outcome, wherein the accuracy of the prediction result calculated by the LSTM is higher than that of the CNN.

In other embodiments, the prediction models of the prediction module 22 could be trained by the historical data of one of the six respiratory parameters (tidal volume, respiratory rate, peak airway pressure, mean airway pressure, positive end-expiratory pressure, and fraction of inspiration $O_2$) and the corresponding extubation outcome. Then, the prediction result is calculated by analyzing data of the respiratory parameters that are the same respiratory parameters used for training the prediction models.

The hospital information system 30 is adapted to receive the prediction result of the patient from the artificial intelligence platform 20 and to record the prediction result that is received into a medical record of the patient. In the current embodiment, the artificial intelligence platform 20 transmits two prediction results to the message queuing apparatus 50, and the hospital information system 30 obtains the two prediction results from the message queuing apparatus 50. In other embodiments, the artificial intelligence platform 20 could transmit the prediction results to the hospital information system 30.

With such design, when a user, such as a doctor, reviews the medical record of the patient through the hospital information system 30, the doctor could learn the prediction result is either the success status or the failure status, and the degree of confidence corresponding to the success status or the failure status. The prediction result calculated by the artificial intelligence platform 20 could be considered by the doctor when the doctor has to determine whether the patient is ready for extubation or not.

In the current embodiment, since two prediction models are utilized to analyze the data of the respiratory parameters to obtain two prediction results, the two prediction results could be used to execute cross-validation. Therefore, the system and the method could provide a prediction result that is more accurate for the doctor's reference during extubation assessment. Additionally, each of the prediction models could analyze the data of the respiratory parameters within one of the different predetermined time periods (such as 3 hours, 2 hours, and 1 hour) to obtain the prediction result. Thus, the prediction results of different predetermined time periods are obtained for being used as a reference for assessing the readiness for extubation.

After the doctor removes the endotracheal tube from the patient, the doctor could enter an extubation outcome of the patient in the hospital information system 30. The extubation outcome of the patient is transmitted to the artificial intelligence platform 20, and the training module 26 utilizes the recorded data of the respiratory parameters of the patient, including the recorded times and the measured values of the respiratory parameters corresponding to each of the recorded times, and the extubation outcome transmitted to the artificial intelligence platform 20 to train each of the prediction models repeatedly, thereby improving the accuracy of each of the prediction model.

In other embodiments, the artificial intelligence platform 20 is not limited to being run on a single server. The artificial intelligence platform 20 could be built in the respiratory assistance device 10, wherein the training module 26 of the artificial intelligence platform 20 is optionally omitted from the respiratory assistance device 10. In such a situation, the prediction model is trained by an artificial intelligence server that is separated from the respiratory assistance device 10. After the prediction model is completely trained, the prediction model is transmitted to the artificial intelligence platform 20 of the respiratory assistance device 10.

In the system and the method for assessing extubation of the current embodiment according to the present invention, the artificial intelligent prediction models are utilized to analyze the date of the respiratory parameters of the patient within the predetermined time period to calculate the prediction results. Comparing the system and the method for assessing extubation of the current embodiment to the conventional index used for assessing extubation, the present invention could present the breathing status of the patient within the predetermined time period before extubation more accurately, thereby providing the reference for assessing the readiness of extubation, which is more accurate. Thus, the prediction result could help the doctor to accelerate the extubation assessment and could shorten the intubation time to reduce the discomfort of the patient.

It must be pointed out that the embodiment described above is only a preferred embodiment of the present invention. All equivalent structures which employ the concepts disclosed in this specification and the appended claims should fall within the scope of the present invention.

What is claimed is:

1. A system for assessing extubation, comprising:
a respiratory assistance device adapted to communicate with a trachea of a patient via an endotracheal tube, wherein the respiratory assistance device continuously records measured values of a plurality of respiratory parameters of the patient at predetermined time intervals;
an artificial intelligence platform receiving recorded times and measured values of the respiratory parameters corresponding to each of the recorded times, wherein the artificial intelligence platform comprises a prediction module, and the prediction module analyzes the measured values of the respiratory parameters within a predetermined time period according to the at least one prediction model and generates at least one prediction result; the at least one prediction result comprises one of a success status and a failure status; and
a hospital information system receiving the at least one prediction result and recording the at least one prediction result that is received into a medical record of the patient.

2. The system for assessing extubation as claimed in claim 1, wherein the at least one prediction result further comprises a degree of confidence that corresponds to the success status or a degree of confidence that corresponds to the failure status.

3. The system for assessing extubation as claimed in claim 1, wherein the at least one prediction model analyzes to calculate the measured values of the respiratory parameters within the predetermined time period based on either convolutional neural network (CNN) or Long short-term memory (LSTM).

4. The system for assessing extubation as claimed in claim 3, wherein the at least one prediction model comprises two prediction models; each of the two prediction models analyzes to calculate the measured values of the respiratory parameters within the predetermined time period based on one of the two algorithms, comprising convolutional neural network (CNN) and Long short-term memory (LSTM), thereby generating two prediction results, respectively; the two prediction results are recorded into the medical record of the patient.

5. The system for assessing extubation as claimed in claim 1, wherein the artificial intelligence platform comprises a training module; the training module trains each of the at least one prediction model by utilizing a plurality of training data; the plurality of training data comprises a plurality of historical data of the respiratory parameters of the reference patients within a reference time period and extubation outcomes of the reference patients.

6. The system for assessing extubation as claimed in claim 5, wherein when an extubation outcome of the patient is entered into the hospital information system, the artificial intelligence platform receives the extubation outcome of the patient that is entered; the training module of the artificial intelligence platform trains the at least one prediction model by utilizing a recorded data of the respiratory of the patient, comprising the recorded times and the measured values of the respiratory parameters corresponding to each of the recorded times, and the extubation outcome of the patient.

7. The system for assessing extubation as claimed in claim 1, wherein the respiratory parameters comprise tidal volume (Vte) and respiratory rate (RR).

8. The system for assessing extubation as claimed in claim 7, wherein the respiratory parameters further comprise at least one of peak airway pressure (Ppeak), mean airway pressure (Pmean), positive end-expiratory pressure (PEEP), and fraction of inspiration $O_2$ ($FiO_2$).

9. The system for assessing extubation as claimed in claim 1, comprising a message queuing apparatus that is respectively connected to the respiratory assistance device, the artificial intelligence platform, and the hospital information system, wherein the recorded times and the measured values of the respiratory parameters corresponding to each of the recorded times recorded by the respiratory assistance device are transmitted to the message queuing apparatus; the artificial intelligence platform obtains the recorded times and the measured values of the respiratory parameters corresponding to each of the recorded times from the message queuing apparatus and transmits the at least one prediction result to the message queuing apparatus; the hospital information system obtains the at least one prediction result from the message queuing apparatus.

10. A method for assessing extubation adapted to be applied to a system for assessing extubation, wherein the system for assessing extubation comprises a respiratory assistance device, an artificial intelligence platform, and a hospital information system; the respiratory assistance device is adapted to communicate with a trachea of a patient; the artificial intelligence platform comprising a prediction module; wherein the method for assessing extubation comprises:

continuously recording measured values of a plurality of respiratory parameters of the patient at predetermined time intervals;

transmitting the recorded time and the measured values of a plurality of respiratory parameters corresponding to the recorded time to the artificial intelligence platform; then, analyzing the measured values of the respiratory parameters within a predetermined time period according to at least one prediction model to generate at least one prediction result by the prediction module, wherein the at least one prediction result comprises one of a success status and a failure status;

transmitting the at least one prediction result to the hospital information system, wherein the hospital information system records the at least one prediction result that is received into a medical record of the patient.

11. The method for assessing extubation as claimed in claim 10, wherein the at least one prediction result further comprises a degree of confidence that corresponds to the success status or a degree of confidence that corresponds to the failure status.

12. The method for assessing extubation as claimed in claim 10, wherein the at least one prediction model analyzes to calculate the measured values of the respiratory parameters within the predetermined time period based on either convolutional neural network (CNN) or Long short-term memory (LSTM).

13. The method for assessing extubation as claimed in claim 12, wherein the at least one prediction model comprises two prediction models; each of the two prediction models analyzes to calculate the measured values of the respiratory parameters within the predetermined time period based on one of the two algorithms, comprising convolutional neural network (CNN) and Long short-term memory (LSTM), thereby generating two prediction results, respectively; the two prediction results are recorded into the medical record of the patient.

14. The method for assessing extubation as claimed in claim 10, wherein the artificial intelligence platform of the system for assessing extubation comprises a training module; the method for assessing extubation further comprises a model training process, wherein the model training process comprises:

receiving a plurality of training data by the training module, and training the at least one prediction model by utilizing the plurality of training data, wherein the plurality of training data comprises a plurality of historical data of the respiratory parameters of the reference patients within a reference time period and extubation outcomes of the reference patients.

15. The method for assessing extubation as claimed in claim 14, wherein the model training process further comprises:

transmitting an extubation outcome of the patient to the artificial intelligence platform, so that the training module of the artificial intelligence platform trains the at least one prediction model by utilizing a recorded data of the respiratory of the patient, comprising the recorded times and the measured values of the respiratory parameters corresponding to each of the recorded times, and the extubation outcome of the patient.

16. The method for assessing extubation as claimed in claim 10, wherein the respiratory parameters comprise tidal volume (Vte) and respiratory rate (RR).

17. The method for assessing extubation as claimed in claim 16, wherein the respiratory parameters further comprise at least one of peak airway pressure (Ppeak), mean airway pressure (Pmean), positive end-expiratory pressure (PEEP), and fraction of inspiration $O_2$ ($FiO_2$).

* * * * *